United States Patent [19]

Malacheski et al.

[11] 4,127,339
[45] Nov. 28, 1978

[54] DISPENSER PACKAGE FOR FLUENT MATERIAL

[76] Inventors: Joseph J. Malacheski; Edward Stelmack, both of 28 E. Division St.; Richard J. Zenda, 21 O'Neill Ave., all of Wilkes-Barre, Pa. 18702

[21] Appl. No.: 733,917

[22] Filed: Oct. 19, 1976

[51] Int. Cl.² .................. B43K 5/14; A61M 35/00
[52] U.S. Cl. .................................. 401/132; 128/260; 128/232; 222/92
[58] Field of Search .............. 222/92, 105, 107, 206, 222/210, 491, 494, 490, 541; D9/182, 192; 206/498, 484; 401/132–134, 201; 128/260, 261, 269, 232, 272

[56] References Cited

U.S. PATENT DOCUMENTS

| 1,816,542 | 7/1931 | Mellin | 206/484 |
|---|---|---|---|
| 2,215,480 | 9/1940 | Sampson | 222/206 |
| 2,489,675 | 11/1949 | Roberts | 128/272 |
| 2,561,071 | 7/1951 | Prisk | 128/260 |
| 2,702,146 | 2/1955 | Land | 222/107 |
| 3,053,385 | 9/1962 | Spees | 206/498 |
| 3,453,661 | 7/1969 | Repko | 222/107 |

FOREIGN PATENT DOCUMENTS 577,611  5/1933  Fed. Rep. of Germany ........... 128/232

Primary Examiner—Robert B. Reeves
Assistant Examiner—H. Grant Skaggs
Attorney, Agent, or Firm—Robert K. Youtie

[57] ABSTRACT

A dispenser package for fluent material, such as viscous fluids, including a flexible applicator sheet for spreading the material, a container carried by the sheet generally centrally thereof for containing the material, and an opening associated with the container for opening the latter to pass the contained fluent material exteriorly of the container for application by the applicator sheet.

2 Claims, 10 Drawing Figures

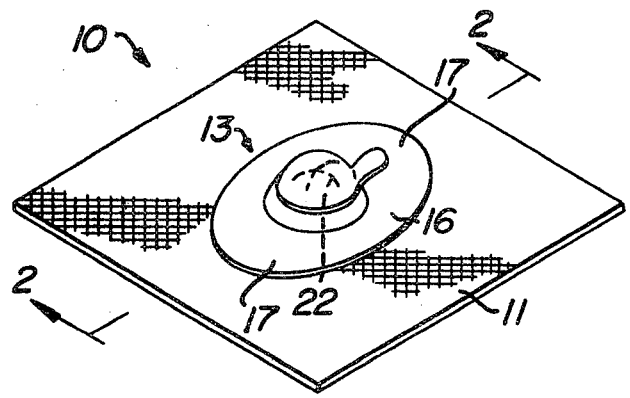
FIG. 1
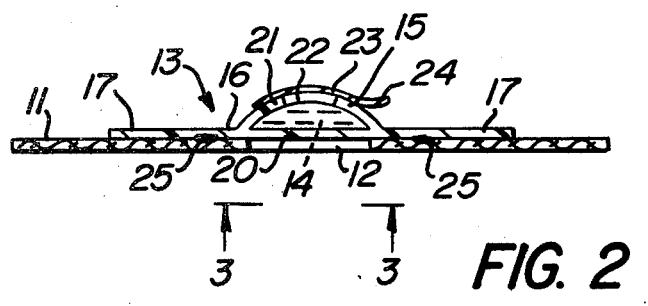
FIG. 2
FIG. 3
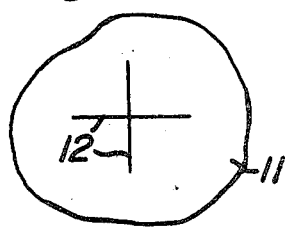
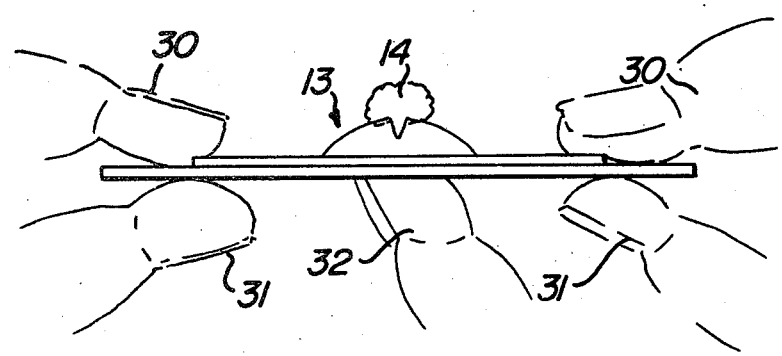
FIG. 4

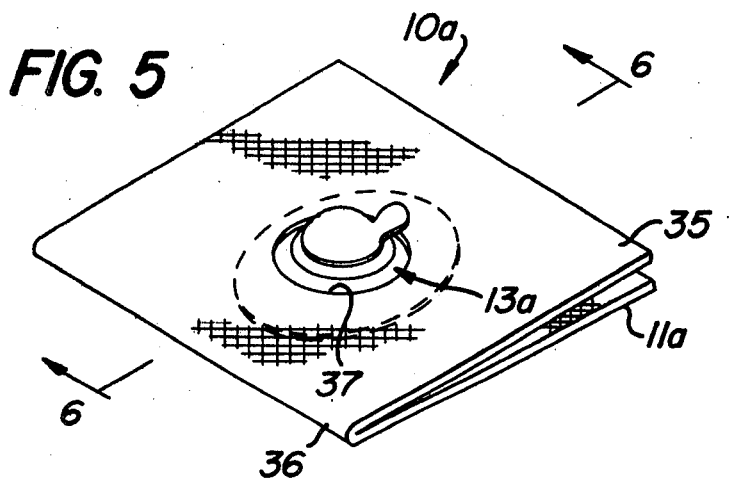
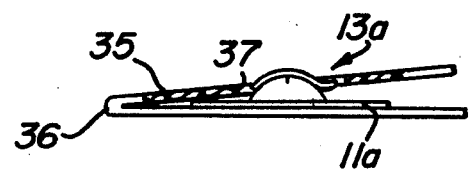
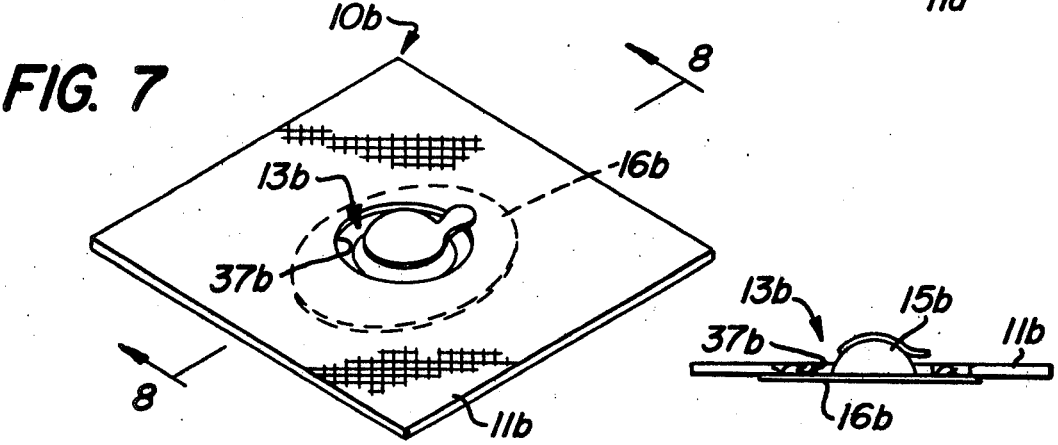
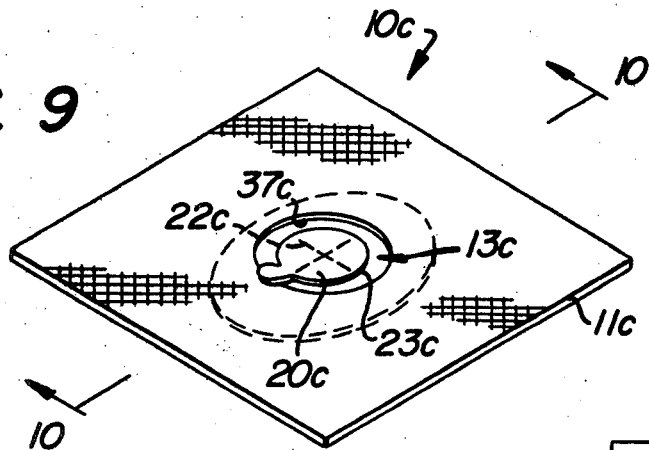
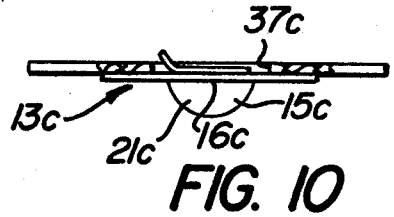

DISPENSER PACKAGE FOR FLUENT MATERIAL

BACKGROUND OF THE INVENTION

While the device of the instant invention is capable of many varied applications, as by mechanics performing maintenance, factory assembly lines, and others, it has been primarily developed for use in topical application of pharmaceuticals. For example, in the application of salves to babies, as well as adults, it is generally necessary to remove salve from a container, as by an applicator or one's fingers, usually involving opening and closing the container, which procedure is inconvenient and messy, as well as tending to lack a desirable degree of sanitation.

SUMMARY OF THE INVENTION

It is, therefore, an important object of the present invention to provide a dispenser package for fluent material which is capable of high sanitation, even in hospital situations, the package being adapted for sterile manufacture and sufficiently economical to justify being discarded after a single use or use on a single patient.

It is a further object of the present invention to provide a dispensing package for fluent material of the type described above which greatly enhances convenience, eliminating the need for separate jars, bottles, tubes or other such bulk containers, avoiding the possibility of contamination inherent in use of bulk containers, and which is extremely simple to use, being capable of use by persons of all ages without special training, and use by professionals as well as patients.

Other objects of the present invention will become apparent upon reading the following specification and referring to the accompanying drawings, which form a material part of this disclosure.

The invention accordingly consists in the features of construction, combinations of elements, and arrangements of parts, which will be exemplified in the construction hereinafter described, and of which the scope will be indicated by the appended claims.

BRIEF DESCRIPTION OF THE DRAWINGS

FIG. 1 is a top perspective view showing a dispenser package constructed in accordance with the teachings of the present invention.

FIG. 2 is a sectional view taken generally along the line 2—2 of FIG. 1.

FIG. 3 is a partial bottom view taken generally along the line 3—3 of FIG. 2.

FIG. 4 is a side elevational view showing the dispenser package of FIGS. 1-3 in an early stage of use.

FIG. 5 is a top perspective view showing a slightly modified embodiment of dispenser package in accordance with the present invention.

FIG. 6 is a sectional view taken generally along the line 6—6 of FIG. 5.

FIG. 7 is a top perspective view showing a further embodiment of the present invention.

FIG. 8 is a sectional view taken generally along the line 8—8 of FIG. 7.

FIG. 9 is a top perspective view showing still another embodiment of the present invention.

FIG. 10 is a sectional view taken generally along the line 10-10 of FIG. 9.

DESCRIPTION OF THE PREFERRED EMBODIMENTS

Referring now more particularly to the drawings, and specifically to FIGS. 1-4 thereof, a dispenser package of the present invention is there generally designated 10, and includes an applicator sheet 11 of flexible sheet material, such as a gauze pad, napkin, or suitable fabric. In the dispensing and application of medicines, it may be advantageous to fabricate the applicator sheet of porous, soft material, but other applications may require applicator sheets of other characteristics. The applicator sheet 11 may be generally rectangular, as illustrated, but may be of other outline configuration if circumstances require.

Generally centrally of the applicator sheet 11, there are formed a pair of crossed slits or cuts 12 which combine to define a finger access passageway, as will appear more fully hereinafter.

On the top surface of applicator sheet 11, as seen in the drawings, there is mounted a container, generally designated 13, which contains fluent material 14, which may be any desired paste, cream, ointment, or the like.

The container 13 is advantageously fabricated of a soft flexible material, such as sheet rubber, latex, or the like, and may include a generally bubble or blister-like enclosure 15 having a circumferentially extending outstanding mounting sheet or flange 16. The central enclosure or blister 15 may be generally circular or disclike, as illustrated, and the surrounding flange 16 is advantageously of elongate or generally ellipsoidal outline configuration to provide extending end portions or tabs 17.

The bubble-like enclosure 15 may overlie the access passageway defining slits 12, and may be constructed to include a generally flat bottom wall 20, and a generally dome-shaped top wall 21 being secured over and in enclosure-forming relation with the bottom wall. The top enclosure wall 21 may have central cuts or slits 22 releasably secured in closed relation by an overlying removable closure or patch 23 having a finger pull or extension tab 24.

Thus, the fluent material 14 is removably retained within the flexible walls 20, 21 of enclosure 15 the slits 22, closure 23 and tab 24 provide opening means.

The surrounding flange 16 may rest on the upper surface of applicator sheet 11, being suitably secured thereto, as by adhesive means, thermoplastic welds, or the like, shown at 25.

In use, it is only required that the user grasp the finger pull or tab 24, pulling the same to remove closure 23. The slits 22 are then free to open under distending pressure, so that the slits combine with closure 23 to define opening means for the enclosure 15.

A quick, easy and sanitary mode of use is shown in FIG. 4, wherein a user's thumbs 30 and index fingers 31 are employed to grasp the package. Specifically, the thumb of each hand bears upon the outer surface of a flange extension or tab 17, while the associated index finger 31 is beneath the applicator sheet 11 to clamp the grasped material between the thumb and index finger. Simultaneously, another finger 32 may enter through the passageway 12, 12 into bearing engagement with the underside of enclosure bottom wall 20, to distend the latter upwardly and express the contents 14 through the opening 22 of enclosure top wall 21. Of course, the fluent material thus discharged exteriorly of the container 13 may be applied by suitable manipulation of the applicator sheet 11.

In FIGS. 5 and 6 is shown a slightly modified embodiment of dispenser package 10a, which may include an applicator sheet 11a and container 13a, similar to the first descirbed embodiment. However, there may be an additional applicator sheet 35, having one edge hingedly connected, as at 36, to one edge of the applicator sheet 11a, and provided with a central through opening or hole 37. The additional applicator sheet 35 is thus swingable about its hinged connection 36 to overlie the first mentioned applicator 11a, in which position the hole 37 receives the upstanding portion of container 13a. By this means, substantially double the area of applicator sheet material may be provided, with but negligible additional space and cost requirements. Of course, the additional applicator sheet 35 may be integral with the first mentioned applicator sheet 11a, as illustrated.

A further embodiment of the instant invention is shown in FIGS. 7 and 8, the dispenser package there being generally designated 10b, and including an applicator sheet 11b, and a container 13b, both of which may be similar to the applicator sheet 11 and container 13 of the first described embodiment. However, the applicator sheet 11b is formed with a central through opening or hole 37b, similar to that of additional applicator sheet opening 37. Also, the container 13b has its circumferential flange 16b beneath and in facing engagement with the underside of applicator sheets 11b, and suitably secured thereto, with the enclosure 15b upstanding through the applicator sheet opening 37b. Thus, the upper surface of container flange 16b is suitably secured in facing engagement with the undersurface of applicator sheet 11b, and the enclosure 15b projects upwardly through and beyond the upper side of the applicator sheet.

This embodiment may be of slightly less thickness, and otherwise advantageous under certain circumstances.

The further embodiment of FIGS. 9 and 10 illustrates a dispenser package 10c, including a generally rectangular applicator sheet 11c having a central through opening or hole 37c. A container 13c includes a circumferential flange 16c suitably secured in facing engagement with the underside of the applicator sheet 11c. The container 13c further includes a bubble-like enclosure 15c located in general registry with the applicator sheet opening 37c and depending away from the applicator sheet, as best seen in FIG. 10. Thus, the enclosure 15c may include a generally flat upper wall 20c generally coplanar with the flange 16c and proximate to the opening 37c, and an inverted dome-shaped bottom wall 21c. The upper, generally flat wall 20c may be provided with opening slits or cuts 22c, releasably retained closed by an openable closure 23c located within the opening 37c.

In this embodiment, the closure 23c may be removed as in the previously described embodiments. However, the depending dome-shaped lower enclosure wall 15c is manually distended upwardly to discharge contents through the slit openings 22c.

From the foregoing description, it will now be apparent that the present invention provides a dispenser package for fluent material which is extremely simple in construction, entirely reliable in operation, and otherwise fully accomplishes its intended objects.

Although the present invention has been described in some detail by way of illustration and example for purposes of clarity of understanding, it is understood that certain changes and modificaitons may be made within the spirit of the invention.

What is claimed is:

1. A dispenser package for fluent material comprising a flexible applicator sheet, a flexible container carried by said applicator sheet and containing fluent material, and container opening means associated with said container for opening the latter to pass said fluent material exteriorly of the container for application by said applicator sheet, said container being mounted on said applicator sheet having one side accessible from one side of said sheet for finger-depression to express the fluent material from the other side of said container on the other side of said applicator sheet, said container comprising an enclosure of flexible sheet material for tactile sensitivity in application, and a flange on said enclosure secured to said applicator sheet and having outwardly extending finger grip portions on opposite sides of said enclosure for holding the enclosure against finger-depression, said container being mounted on said other side of said sheet, and said applicator sheet having a passageway affording said finger access.

2. A dispenser package for fluent material according to claim 1, said opening means comprising cuts in said enclosure, a closure removably secured to said enclosure in closing relation with said cuts, and a finger pull on said closure for removing the latter.

* * * * *